US011992297B2

United States Patent
Kwon et al.

(10) Patent No.: US 11,992,297 B2
(45) Date of Patent: May 28, 2024

(54) MONITORING METHOD OF HEART RATE FOR TOXICITY TEST USING HIGH-SPEED DIGITAL HOLOGRAPHY

(71) Applicant: KOREA RESEARCH INSTITUTE OF STANDARDS AND SCIENCE, Daejeon (KR)

(72) Inventors: Ik Hwan Kwon, Gimpo-si (KR); Tae Geol Lee, Daejeon (KR); Sang Won Lee, Sejong-si (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 676 days.

(21) Appl. No.: 17/164,686

(22) Filed: Feb. 1, 2021

(65) Prior Publication Data

US 2021/0251183 A1 Aug. 19, 2021

(30) Foreign Application Priority Data

Feb. 3, 2020 (KR) .................. 10-2020-0012385
Nov. 2, 2020 (KR) .................. 10-2020-0144571

(51) Int. Cl.
*A61B 5/00* (2006.01)
*A01K 1/03* (2006.01)
(Continued)

(52) U.S. Cl.
CPC .............. *A61B 5/024* (2013.01); *A01K 1/031* (2013.01); *A01K 61/00* (2013.01); *A61D 3/00* (2013.01);
(Continued)

(58) Field of Classification Search
CPC .................................................. G03H 1/0443
See application file for complete search history.

(56) References Cited

U.S. PATENT DOCUMENTS

2009/0232739 A1* 9/2009 Cheng ................ G01N 33/5014
424/9.2
2012/0218379 A1* 8/2012 Ozcan .................. G03H 1/0443
348/40
(Continued)

FOREIGN PATENT DOCUMENTS

| CN | 102716501 | * | 3/2011 | ............. A61K 49/00 |
| CN | 109556487 | * | 11/2018 | ............... G01B 5/02 |

(Continued)

OTHER PUBLICATIONS

Donnarumma, D., Brodoline, A., Alexandre, D., & Gross, M. (2016). Blood flow imaging in zebrafish by laser Doppler digital holography. Microscopy Research and Technique, 81(2), 153-161 (Year: 2016).*

(Continued)

*Primary Examiner* — John R Downey
*Assistant Examiner* — Anant A Gupta
(74) *Attorney, Agent, or Firm* — McCoy Russell LLP

(57) ABSTRACT

Provided is a method of monitoring a heart rate of an open circulatory system aquatic organism including water fleas, zebrafish, brine shrimp, and the method of evaluating individual response by real time measurement of a heart rate of an aquatic organism and the individual response evaluation apparatus by real time measurement of a heart rate of an aquatic organism according to the present invention may effectively fix the aquatic organism for real time measurement of the heart rate of an aquatic organism, and may measure the heart rate using digital holography to display the heart rate while configuring a data format to allow the corresponding data to be stored for a long time, thereby treating a compound for inducing an individual response, securing a heart rate change in real time by image processing, and then effectively determining the presence or (Continued)

absence of harmfulness due to induction of the individual response.

13 Claims, 8 Drawing Sheets

(51) Int. Cl.
    *A01K 61/00*      (2017.01)
    *A61B 5/024*      (2006.01)
    *A61D 3/00*      (2006.01)
    *G03H 1/04*      (2006.01)

(52) U.S. Cl.
    CPC ........ *G03H 1/0443* (2013.01); *A61B 2503/40* (2013.01)

(56) References Cited

U.S. PATENT DOCUMENTS

| | | | | |
|---|---|---|---|---|
| 2015/0011844 | A1* | 1/2015 | Paradis | A61B 8/08 600/301 |
| 2015/0315546 | A1* | 11/2015 | Sinha | C12N 15/02 435/6.12 |

FOREIGN PATENT DOCUMENTS

| | | | | |
|---|---|---|---|---|
| CN | 109556487 | * | 4/2019 | ............... G01B 5/02 |
| JP | 2007528485 A | | 10/2007 | |

OTHER PUBLICATIONS

Gao, J., Lyon, J. A., Szeto, D. P., & Chen, J. (2012). In vivo imaging and quantitative analysis of zebrafish embryos by digital holographic microscopy. Biomedical Optics Express, 3(10), 2623. https://doi.org/10.1364/boe.3.002623. (Year: 2012).*

Lovern, S. et al., "Behavioral and physiological changes in Daphnia magna when exposed to nanoparticle suspensions (titanium dioxide, nano-C60, and C60HxC70Hx)," Environmental Science Technology, vol. 41, No. 12, Jun. 15, 2007, 12 pages.

Kim, B. et al., "Stimulus-Responsive Anti-Oxidizing Drug Crystals and Its Ecological Implication," Small, vol. 15, No. 21, Available Online Apr. 5, 2019, May 2019, 25 pages.

Donnarumma, D. et al., "Blood Flow Imaging in Zebrafish by Laser Doppler Digital Holography," Microscopy Research and Technique, vol. 81, No. 2, Feb. 2018, Available Online May 7, 2016, 9 pages.

Korean Intellectual Property Office, Office Action Issued in Application No. 2020-0144571, dated Dec. 30, 2021, 11 pages.

* cited by examiner

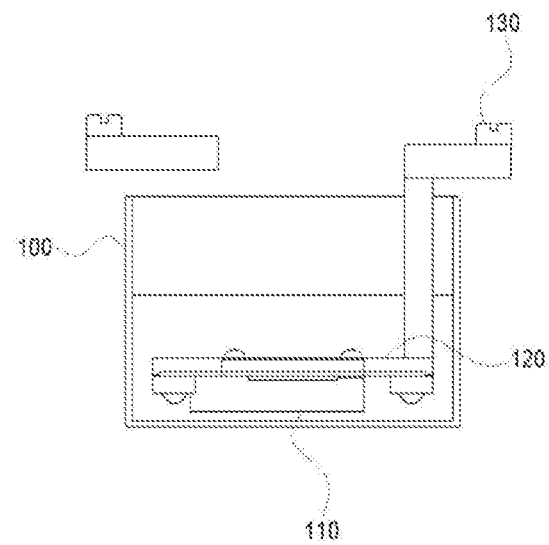
FIG. 2
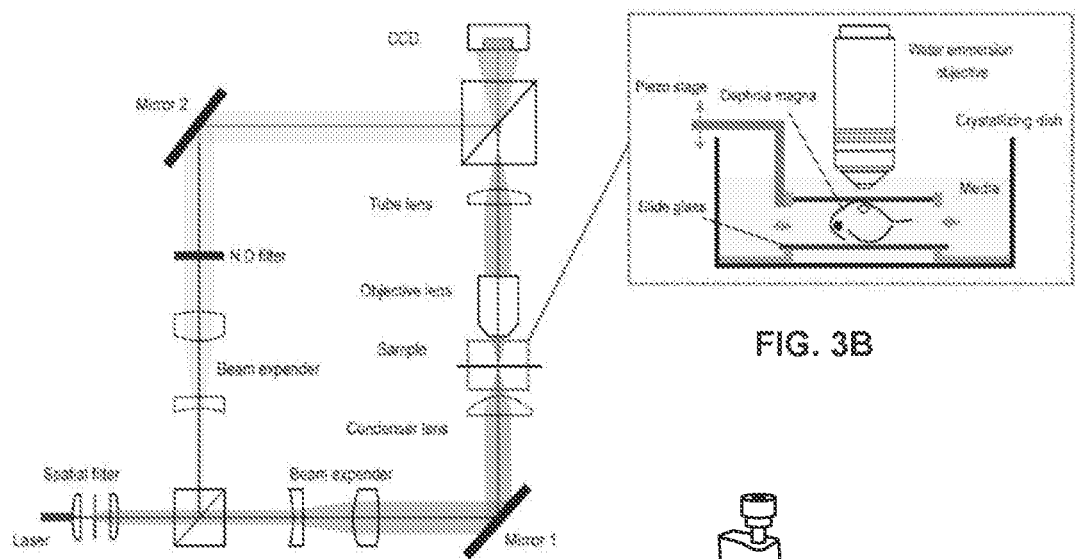
FIG. 3A
FIG. 3B
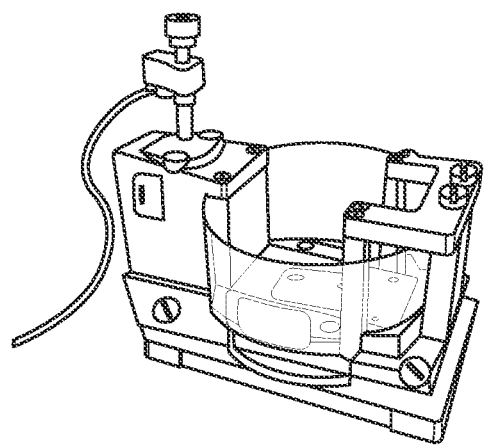
FIG. 3C

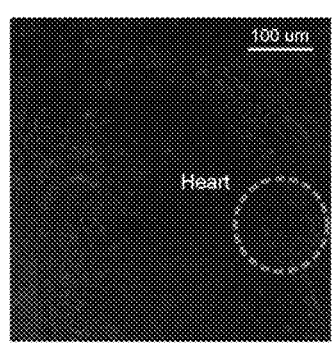
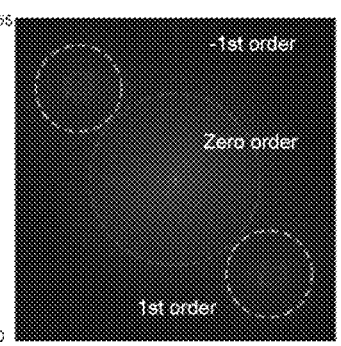
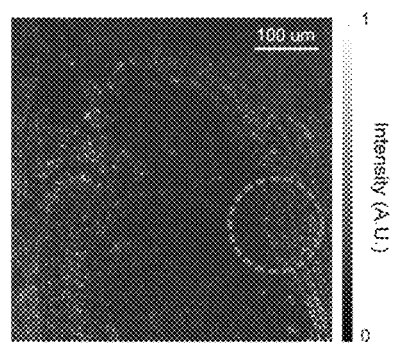
FIG. 4A　　　　FIG. 4B　　　　FIG. 4C
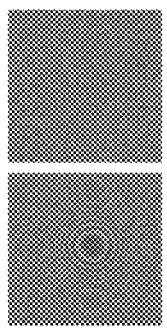
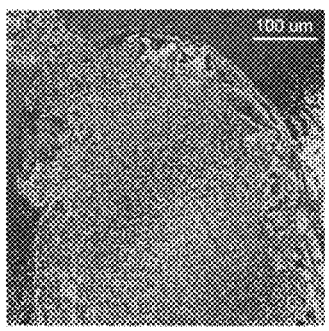
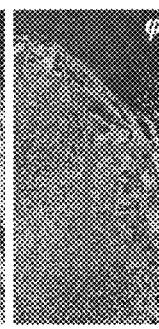
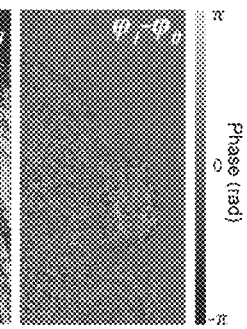
FIG. 4D　　FIG. 4E　　FIG. 4F　　FIG. 4G　　FIG. 4H

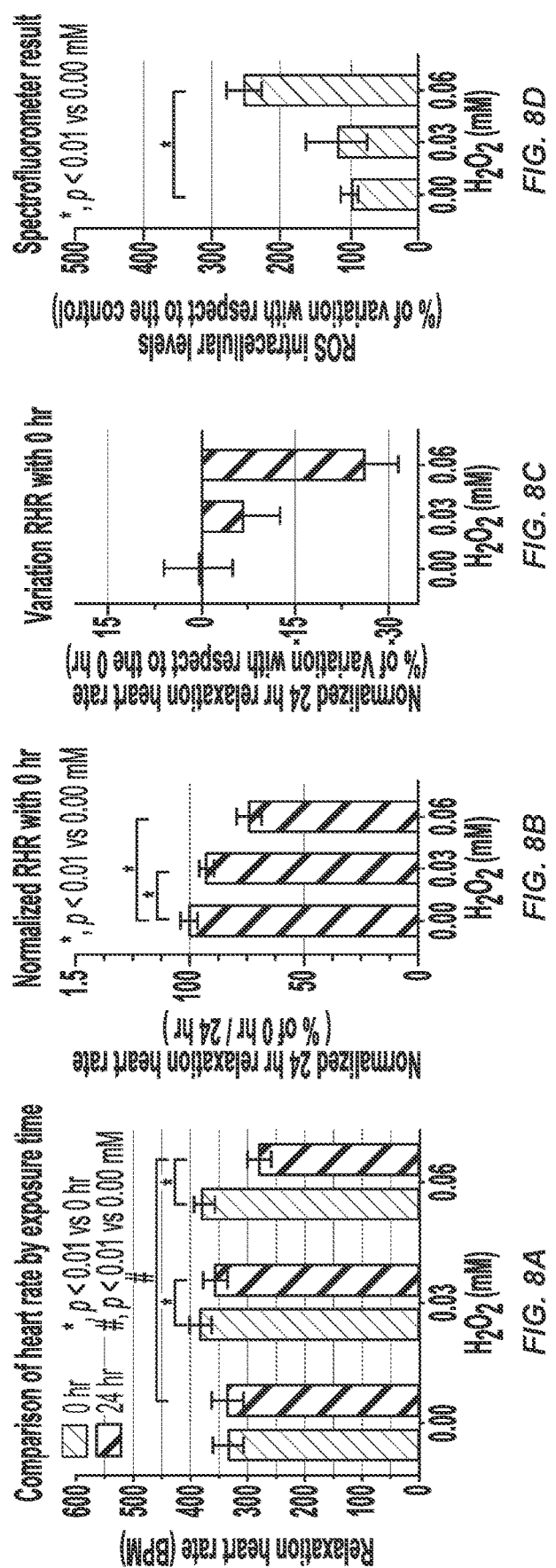

MONITORING METHOD OF HEART RATE FOR TOXICITY TEST USING HIGH-SPEED DIGITAL HOLOGRAPHY

CROSS REFERENCE TO RELATED APPLICATIONS

The present application claims priority to Korean Patent Application No. 10-2020-0012385 filed on Feb. 3, 2020 and Korean Patent Application No. 10-2020-0144571 filed on Nov. 2, 2020. The entire contents of the above-listed applications are hereby incorporated herein by reference for all purposes.

TECHNICAL FIELD

The following disclosure relates to a method of monitoring a heart rate for a toxicity test using high-speed digital holography, and more particularly, to a method of monitoring a heart rate of an open circulatory system aquatic organism including water fleas, zebrafish, and brine shrimp.

BACKGROUND

Dynamic behavior change of aquatic organisms such as zebrafish or a water flea has been widely studied in the field of ecotoxicology, environmental safety, nanodynamics, and the like. A water flea is appropriate in a micro-sized biotest, due to a possibility of cultivation in a large number in a small place and a short growth time. In addition, since their culture environment is indicated in international standard aquatic toxicity assessment guidelines, the water flea has also served as an advantage for cooperative studies. Cardiac toxicity assessment using water fleas has had an interesting result for nanoparticles or reactive oxygen species, and a heart rate change using water fleas may not be the same as that of humans, but an effect of a compound or nanoparticles on a general metabolic process such as an antioxidation drug test may be confirmed.

The heart rate of water fleas disposed in a medium immersed in a small amount on a Petri dish or a well plate was usually observed by the naked eye through a microscope, and is still widely used. Since the method has a problem of low accuracy depending on the experimenter's dynamic vision, improvement therefor is needed. Recently, a phase microscope is used to solve the problem, but which is inappropriate since images produced during a long-term experiment occupy computer memory and data storage on a vast scale, and thus, there is a desperate need for improvement therefor.

RELATED ART DOCUMENTS

Non-Patent Documents

Lovern S B et al. Behavioral and Physiological Behavioral and Physiological Changes in *Daphnia magna* when Exposed to Nanoparticle Suspensions (Titanium Dioxide, Nano-C 60, and C 60 HxC 70 Hx). Environ. Sci. Technol. 41, 4465-4470 (2007).

Kim B S et al., Stimulus-Responsive Anti-Oxidizing Drug Crystals and their Ecological Implication. Small 15, 1-11 (2019).

SUMMARY

An embodiment of the present invention is directed to providing a method of evaluating an individual response by real time measurement of a heart rate, which allows real time measurement of a heart rate of an aquatic organism for a long time and monitoring thereof.

Another embodiment of the present invention is directed to providing a chamber in which an underwater environment is simulated, which naturally fixes movement of aquatic organisms, and an individual response evaluation apparatus by real time measurement of a heart rate of an aquatic organism.

In one general aspect, a method of evaluating an individual response by real time measurement of a heart rate of an aquatic organism which is a method of evaluating an individual response using digital holography, includes: (a) disposing a measurement individual between a lower fixing unit fixed to a lower end inside a chamber and an upper fixing unit which is spaced apart from the lower fixing unit and is movable in a direction of the lower fixing unit or in an opposite direction thereof so that the measurement individual is immersed in a culture fluid to which a compound for inducing an individual response is added, closely adhering the upper fixing unit to the individual to measure a height of the individual, and then adjusting a position of the upper fixing unit to fix the individual; (b) continuously measuring a digital hologram for the individual; and (c) restoring the digital hologram obtained by the measurement to calculate a heart rate change, and determining therefrom whether the individual response is caused by the compound for inducing an individual response.

In the method of evaluating an individual response by real time measurement of a heart rate of an aquatic organism according to an exemplary embodiment of the present invention, the step (a) may include disposing an individual to be measured between a lower fixing unit fixed to a lower end inside a chamber carrying a culture fluid and an upper fixing unit which is spaced apart from the lower fixing unit and is movable in a direction of the lower fixing unit or in an opposite direction thereof so that the individual to be measured is immersed in the fluid, closely adhering the upper fixing unit to the individual to measure a height of the individual, and then adjusting a position of the upper fixing unit to fix the individual; and adding a compound for inducing the individual response to the chamber.

In the method of evaluating an individual response by real time measurement of a heart rate of an aquatic organism according to an exemplary embodiment of the present invention, the step (a) may include disposing an individual to be measured between a lower fixing unit fixed to a lower end inside a chamber carrying a culture fluid to which a compound for inducing an individual response is added and an upper fixing unit which is spaced apart from the lower fixing unit and is movable in a direction of the lower fixing unit or in an opposite direction thereof so that the individual to be measured is immersed in the fluid, closely adhering the upper fixing unit to the individual to measure a height of the individual, and then adjusting a position of the upper fixing unit to fix the individual.

In the method of evaluating an individual response by real time measurement of a heart rate of an aquatic organism according to an exemplary embodiment of the present invention, after adjusting the position of the upper fixing unit to fix the individual, a distance between the lower fixing unit and the upper fixing unit may be a ratio of 0.92 to 0.95 relative to the height of the individual to be measured.

In the method of evaluating an individual response by real time measurement of a heart rate of an aquatic organism according to an exemplary embodiment of the present invention, the compound may be an organic compound, a metal, acid-alkali, gas, a medicine, or a nanoparticle.

In the method of evaluating an individual response by real time measurement of a heart rate of an aquatic organism according to an exemplary embodiment of the present invention, the compound may be selected from dimethylformamide, methanol, methylisobutylketone, benzene, carbon tetrachloride, styrene, cyclohexane, acetone, acetaldehyde, isobutylalcohol, methyl chloride, ethylene glycol, xylene, toluene, toluene-2,4-diisocyanate, trichloroethylene, n-hexane, lead, nickel, manganese, mercury, zinc, aluminum, iron, cadmium, chromium, hydrogen peroxide, acetic acid, sodium hydroxide, hydrochloric acid, sulfuric acid, nitric acid, phosphoric acid, ammonia, chlorine, ozone, hydrogen sulfide, carbon monoxide, sulfur dioxide, nitrogen dioxide, medicines, gold nano, silver nano, single-walled carbon nanotubes (SWCNT), multi-walled carbon nanotube (MWCNT), fullerene ($C_{60}$), iron nanoparticles, carbon black, titanium dioxide, aluminum oxide, cerium oxide, zinc oxide, silicon dioxide, polystyrene, dendrimers, and nanoclay.

In the method of evaluating an individual response by real time measurement of a heart rate of an aquatic organism according to an exemplary embodiment of the present invention, the individual may be treated with the compound at a concentration of 0.01 to 0.10 mM.

In the method of evaluating an individual response by real time measurement of a heart rate of an aquatic organism according to an exemplary embodiment of the present invention, the algorithm for restoration may further include displaying a 2D-time-resolved relative phase map in real time and storing the heart rate at the same time.

In the method of evaluating an individual response by real time measurement of a heart rate of an aquatic organism according to an exemplary embodiment of the present invention, the heart rate may be obtained by an analysis method including a) selecting pixels corresponding to a heart area in the secured digital hologram; b) applying a Fourier spectrum method to each refreshing interval; c) searching a most frequent heart rate in each refreshing interval; and d) calculating a heart rate per minute from the most frequent heart rate.

In the method of evaluating an individual response by real time measurement of a heart rate of an aquatic organism according to an exemplary embodiment of the present invention, the step of applying a Fourier spectrum method may be obtained based on a value by a k-space angular spectrum method by the following Equations:

$$H(x, y, z) = \frac{1}{2\pi} \int\int_z dx_0 dy_0 H_0(x_0, y_0) F^{-1}\left\{\exp\left[i\left(\sqrt{(k^2 - k_x^2) + (k^2 - k_y^2)}\right)z\right]\right\}$$
$$= H_0 \otimes T$$

$$T(x, y, z) = \frac{1}{2\pi} F^{-1}\left\{\exp\left(ikz\sqrt{k^2 - k_x^2 - k_y^2}\right)\right\}.$$

Equation II $$A(x, y) = \text{Re}|H(x, y; z)|^2 + \text{Im}|H(x, y; z)|^2$$

$$\varphi(x, y) = \tan^{-1}\left\{\frac{\text{Im}|H(x, y; z)|}{\text{Re}|H(x, y; z)|}\right\}.$$

Equation III

In the method of evaluating an individual response by real time measurement of a heart rate of an aquatic organism according to an exemplary embodiment of the present invention, the heart rate change may be obtained by calculating an original heart rate (OHR), and a relaxation heart rate (RHR) by the following Equation:

$$RHR = \frac{\sum_{j=t_i}^{t_f} OHR(j)}{t_f - t_i}.$$

Equation IV wherein $t_i$ and $t_f$ refer to an initial time domain and a final time domain in a relaxation state.

In another general aspect, an individual response evaluation apparatus by real time measurement of a heart rate of an aquatic organism is an individual response evaluation apparatus by real time measurement of a heart rate of an aquatic organism using a digital hologram including: a chamber carrying a culture fluid; a lower fixing unit; an upper fixing unit spaced apart from the lower fixing unit; and a control unit controlling a position of the upper fixing unit, wherein the lower fixing unit is fixed to a lower end inside the chamber, an individual to be measured is disposed between the lower fixing unit and the upper fixing unit, the upper fixing unit is fixed to one side surface of the chamber and movable up and down, and the control unit adjusts the position of the upper fixing unit to fix the individual, after the upper fixing unit is closely adhered to the individual to measure the height the individual.

In the individual response evaluation apparatus by real time measurement of a heart rate of an aquatic organism according to an exemplary embodiment of the present invention, the individual response evaluation apparatus may further include: a light source unit; a reference beam generating unit which produces a reference beam; an object beam generating unit which produces an object beam; a CCD(Charge-coupled device) which combines the reference beam and the object beam to record a hologram; an arithmetic unit which numerically analyzes an interference fringe of the recorded hologram; a display unit which displays the digital hologram numerically analyzed by the arithmetic unit; and a heart rate analysis unit which carries out heart rate analysis from the analyzed digital hologram, wherein the arithmetic unit may obtain a plurality of phase restoration phases for the hologram recorded in the CCD, and calculate an amplitude and an angle therefrom and transfer them to the display unit, the display unit may display the restoration image of the hologram recorded in the CCD in real time and transfer it to the heart rate analysis unit, and in the heart rate analysis, a heart rate per minute may be calculated from the most frequent heart rate.

In the individual response evaluation apparatus by real time measurement of a heart rate of an aquatic organism according to an exemplary embodiment of the present invention, the control unit may adjust a distance between the lower fixing unit and the upper fixing unit to a ratio of 0.87 to 0.95 relative to the height of the individual to be measured.

In the individual response evaluation apparatus by real time measurement of a heart rate of an aquatic organism according to an exemplary embodiment of the present invention, the control unit may adjust a distance between the lower fixing unit and the upper fixing unit to a ratio of 0.92 to 0.95 relative to the height of the individual to be measured.

In the individual response evaluation apparatus by real time measurement of a heart rate of an aquatic organism according to an exemplary embodiment of the present invention, the individual response evaluation apparatus may measure one or more data selected from the group consisting of a real time heart rate of an aquatic organism, a spaced interval between the lower fixing unit and the upper fixing unit, a real time display of a time difference relative phase image, and a relaxation heart rate at the same time.

In the individual response evaluation apparatus by real time measurement of a heart rate of an aquatic organism according to an exemplary embodiment of the present invention, the data measured at the same time by the individual response evaluation apparatus may be accumulated by iterative learning by applying an artificial intelligence method.

In the individual response evaluation apparatus by real time measurement of a heart rate of an aquatic organism according to an exemplary embodiment of the present invention, the individual response evaluation apparatus may be used for predicting a heart rate change in a higher organism by the iterative learning.

Other features and aspects will be apparent from the following detailed description, the drawings, and the claims.

BRIEF DESCRIPTION OF THE FIGURES

FIG. 2 is a drawing for a chamber configuration which is a core element of the individual response evaluation apparatus for real time measurement of a heart rate of an aquatic organism according to the present invention.

FIGS. 3A-3C are a schematic diagram of the method of evaluating an individual response by real time measurement of a heart rate of an aquatic organism according to the present invention and a schematic diagram for an embodiment, in which 3(A) is a holography configuration example based on a Mach Zehnder interferometer, which is extra-axial digital holography, 3(B) is a chamber, and 3(C) is an implemented hardware of an individual response apparatus for real time measurement of a heart rate of an aquatic organism.

FIGS. 4A-4H relates to a numerical reconstruction process of digital holography using a spatial filter method, in the method of evaluating an individual response by real time measurement of a heart rate of an aquatic organism according to the present invention.

FIGS. 8A-8D are results of analyzing a relaxation heart rate (RHR) 24 hours after exposure by concentration, by the method of evaluating an individual response by real time measurement of a heart rate of an aquatic organism according to the present invention.

DETAILED DESCRIPTION OF MAIN ELEMENTS

Figure 1:
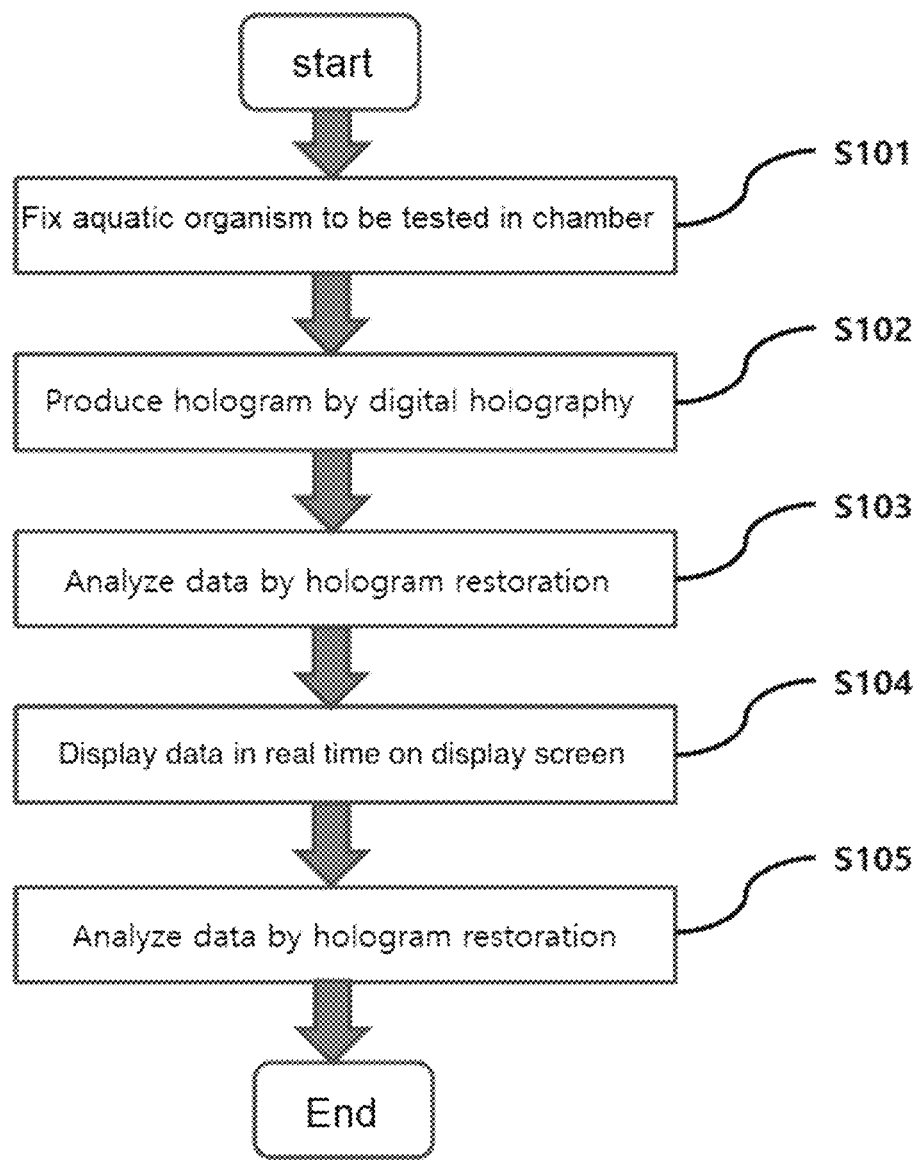
FIG. 1 is a flow chart for the method of evaluating an individual response by real time measurement of a heart rate of an aquatic organism according to the present invention.

S101: Installation step
S102: Image secure step
S103: Data processing step
S104: Display step
S105: Heart rate analysis step
100: Chamber
110: Lower fixing unit
120: Upper fixing unit
130: Control unit

DETAILED DESCRIPTION

Hereinafter, the method of evaluating an individual response by real time measurement of a heart rate of an aquatic organism of the present invention will be described in detail with reference to the accompanying table or drawings.

When a drawing is illustrated, the drawing is provided by way of example so that the idea of the present invention may be sufficiently conveyed to a person skilled in the art. Therefore, the present invention is not limited to the provided drawings, but may be embodied in many different forms, and the drawings may be exaggerated in order to clear the spirit of the present invention.

Terms such as "first" and "second" may be used to describe various constitutional elements, but the constitutional elements are not limited by the terms. The terms are used only to distinguish one constitutional element from another constitutional element. For example, a first constitutional element may be named a second constitutional element and the second constitutional element may also be similarly named the first constitutional element, without departing from the scope of the present invention.

Technical terms and scientific terms used herein have the general meaning understood by those skilled in the art to which the present invention pertains unless otherwise defined, and a description for the known function and configuration which may unnecessarily obscure the gist of the present invention will be omitted in the following description and the accompanying drawings. It must be understood that the terms defined by the dictionary are identical with the meanings within the context of the related art, and they should not be ideally or excessively formally defined unless the context clearly dictates otherwise.

In addition, the singular form used in the specification of the present invention may be intended to also include a plural form, unless otherwise indicated in the context.

In addition, units used in the specification of the present invention without particular mention are based on weights, and as an example, a unit of % or ratio refers to a wt % or a weight ratio.

In addition, in the specification of the present invention, the expression "comprise" is an open-ended description having a meaning equivalent to the expression such as "provided", "contain", "have", or "is/are characterized", and does not exclude elements, materials or processes which are not further listed. In addition, the expression "substantially consisting of . . . " means that other elements, materials, or processes which are not listed together with specified elements, materials, or processes may be present in an amount which does not have an unacceptable significant influence on at least one basic and novel technical idea of the invention. In addition, the expression "consisting of" means that only the described elements, materials, or processes are present.

The term used in the specification of the present invention, "component", "composition", "composition of a compound", "compound", "drug", "pharmaceutical activator", "cure", "treatment", or "medicine" is interchangeably used for meaning a compound or a composition of a compound(s) or a material inducing a desired pharmaceutical and/or physiological effect by a topical and/or systemic action when administrating it to a subject (human or animal).

In the present invention, "sample" or "specimen" represents a subject to be analyzed, and is used in the same sense throughout the specification.

Hereinafter, the present invention will be described in detail by way of example. The examples are only for describing the present invention in more detail, and the scope of the present invention is not limited to the following Examples.

Hereinafter, the method of evaluating an individual response by real time measurement of a heart rate of an aquatic organism of the present invention will be described in detail.

The method of evaluating an individual response by real time measurement of a heart rate of an aquatic organism according to the present invention which is a method of evaluating an individual response using digital holography, includes: (a) disposing a measurement individual between a lower fixing unit fixed to a lower end inside a chamber and an upper fixing unit which is spaced apart from the lower fixing unit and is movable in a direction of the lower fixing unit or in an opposite direction thereof so that the measurement individual is immersed in a culture fluid to which a compound for inducing an individual response is added, closely adhering the upper fixing unit to the individual to measure a height of the individual, and then adjusting a position of the upper fixing unit to fix the individual; (b) continuously measuring a digital hologram for the individual; and (c) restoring the digital hologram obtained by the measurement to calculate a heart rate change, and determining therefrom whether the individual response is caused by the compound for inducing an individual response.

The step (a) may include disposing an individual to be measured between a lower fixing unit fixed to a lower end inside a chamber carrying a culture fluid and an upper fixing unit which is spaced apart from the lower fixing unit and is movable in a direction of the lower fixing unit or in an opposite direction thereof so that the individual to be measured is immersed in the fluid, closely adhering the upper fixing unit to the individual to measure a height of the individual, and then adjusting a position of the upper fixing unit to fix the individual; and adding a compound for inducing the individual response to the chamber, and in addition, the step (a) may include disposing an individual to be measured between a lower fixing unit fixed to a lower end inside a chamber carrying a culture fluid to which a compound for inducing an individual response is added and an upper fixing unit which is spaced apart from the lower fixing unit and is movable in a direction of the lower fixing unit or in an opposite direction thereof so that the individual to be measured is immersed in the fluid, closely adhering the upper fixing unit to the individual to measure a height of the individual, and then adjusting a position of the upper fixing unit to fix the individual.

Here, after the position of the upper fixing unit is adjusted and fixed, a distance between the lower fixing unit and the upper fixing unit may be a ratio of 0.87 to 0.95, preferably 0.89 to 0.95, and more preferably 0.92 to 0.95 relative to the height of the individual to be measured.

The compound may be an organic compound, a metal, acid-alkali, gas, a medicine, or a nanoparticle, and according to a more specific exemplary embodiment, may be selected from dimethylformamide, methanol, methylisobutylketone, benzene, carbon tetrachloride, styrene, cyclohexane, acetone, acetaldehyde, isobutylalcohol, methyl chloride, ethylene glycol, xylene, toluene, toluene-2,4-diisocyanate, trichloroethylene, n-hexane, lead, nickel, manganese, mercury, zinc, aluminum, iron, cadmium, chromium, hydrogen peroxide, acetic acid, sodium hydroxide, hydrochloric acid, sulfuric acid, nitric acid, phosphoric acid, ammonia, chlorine, ozone, hydrogen sulfide, carbon monoxide, sulfur dioxide, nitrogen dioxide, medicines, gold nano, silver nano, single-walled carbon nanotubes (SWCNT), multi-walled carbon nanotube (MWCNT), fullerene ($C_{60}$), iron nanoparticles, carbon black, titanium dioxide, aluminum oxide, cerium oxide, zinc oxide, silicon dioxide, polystyrene, dendrimers, nanoclay, and the like, but is not limited thereto, and may be appropriately selected and used regardless of the type, as long as cytotoxicity for the individual may be measured.

A concentration of the compound at the time of treatment is not particularly limited, but as a specific example, the individual may be treated with the compound at a concentration of 0.001 to 0.50 mM, preferably 0.005 to 0.40 mM, and more preferably 0.01 to 0.10 mM.

The algorithm for restoration may further include displaying a 2D-time-resolved relative phase map in real time and storing the heart rate at the same time.

The heart rate may be obtained by an analysis method including a) selecting pixels corresponding to a heart area in the secured digital hologram; b) applying a Fourier spectrum method to each refreshing interval; c) searching a most frequent heart rate in each refreshing interval; and d) calculating a heart rate per minute from the most frequent heart rate.

The secured digital hologram I(x,y) represents an optical interference signal between an object beam and an interference. By the spatial masking method according to an exemplary embodiment of the present invention, an object wave-field by a two-dimensional fast Fourier transform (FFT) method of a hologram image is defined.

$$I(x, y) = |U_o + U_r|^2 \quad \text{Equation 1}$$
$$= U_o U_o^* + U_r U_r^* + U_o U_r^* + U_r U_o^*$$

wherein $U_o$ and $U_r$ represent a wave-field of an object and an interference, respectively, and an asterisk (*) is related to a complex conjugate value. Among four terms constituting Equation 1, the former two terms represent autocorrelation terms, the third term represents a real image term, and the fourth term represents a virtual image term, respectively. The application of the method is described in (B) of FIG. 4 according to an exemplary embodiment of the present invention.

The object wave-field depending on a distance z in the hologram may be mathematically calculated using an angular spectrum method, and the method may be obtained by a wave propagation technique by a hologram plane H and a phase propagation factor exp[ikz] obtained by Fourier transform.

A step of applying the Fourier spectrum method may be obtained based on a value by a k-space angular spectrum method by the following Equation:

Equation II $$H(x, y; z) = \frac{1}{2\pi} \int\int_z dx_0 dy_0 H_0(x_0, y_0) F^{-1}\left\{\exp\left[i\left(\sqrt{(k^2 - k_x^2) + (k^2 - k_y^2)}z\right)\right]\right\}$$
$$= H_0 \otimes T$$

$$T(x, y, z) = \frac{1}{2\pi} F^{-1}\left\{\exp\left(ikz\sqrt{k^2 - k_x^2 - k_y^2}\right)\right\}.$$

Equation III $$A(x, y) = \text{Re}|H(x, y; z)|^2 + \text{Im}|H(x, y; z)|^2$$

$$\varphi(x, y) = \tan^{-1}\left\{\frac{\text{Im}|H(x, y; z)|}{\text{Re}|H(x, y; z)|}\right\}.$$

The heart rate change may be obtained by calculating an original heart rate (OHR) and a relaxation heart rate (RHR) by the following Equation 1:

Equation IV $$RHR = \frac{\sum_{j=t_i}^{t_f} OHR(j)}{t_f - t_i},$$

wherein $t_i$ and $t_f$ refer to an initial time domain and a final time domain in a relaxation state.

Among various qualitative phase imaging methods, digital holographic microscopy (DHM) may reconstruct geographic information expressed in a complicated amplitude including an amplitude and phase information of an object wave field in an interference image. Since an ability of a digital holographic microscope may produce reconstructed phase information for a refractive index distribution present in a biological sample given by a high-speed camera.

FIG. 1 illustrates a schematic flow chart of the method of evaluating an individual response by real time measurement of an aquatic organism.

Referring to the drawing, the method of evaluating an individual response by real time measurement of an aquatic organism includes an installation step (S101), an image secure step (S102), a data arithmetic operation step (S103), a display step (S104), and a heart rate analysis step (S105).

The installation step (S101) is a step of disposing an aquatic organism to be tested between a lower fixing unit inside a chamber and an upper fixing unit and fixing the aquatic organism. After completing the installation step (S101), continuous images of the aquatic organism is obtained by digital holographic microscopy to create a hologram.

The image secure step (S102) includes taking an optical interference signal produced from an object beam passing through an individual and a reference beam irradiated from a light source unit with a unit such as a CCD camera, thereby producing a hologram. The light source unit is operated to produce the object beam and the reference beam and the optical interference signal produced by a beam splitter is taken to obtain a hologram image.

In the data arithmetic operation step (S103), the obtained hologram image is restored to obtain a complex amplitude value. Here, a method of calculating an amplitude and a phase angle of the complex amplitude is not particularly limited, but as an example, an angular spectrum method may be applied. A time difference phase value for the data restored by the method is calculated.

In the display step (S104), the data restored in the data arithmetic operation step is received and displayed on a display screen in real time, and when it corresponds to a heart area, the data transferred to a heart rate analysis step to be utilized in calculation of the heart rate per minute.

In the heart rate analysis step (S105), a data determined as corresponding to the heart area in the display step (S104) is received to calculate the heart rate per minute.

The individual response evaluation apparatus by real time measurement of a heart rate of an aquatic organism according to the present invention is an individual response evaluation apparatus by real time measurement of a heart rate of an aquatic organism using a digital hologram including: a chamber carrying a culture fluid; a lower fixing unit; an upper fixing unit spaced apart from the lower fixing unit; and a control unit controlling a position of the upper fixing unit, wherein the lower fixing unit is fixed to a lower end inside the chamber, an individual to be measured is disposed between the lower fixing unit and the upper fixing unit, the upper fixing unit is fixed to one side surface of the chamber and movable up and down, and the control unit adjusts the position of the upper fixing unit to fix the individual, after the upper fixing unit is closely adhered to the individual to measure the height the individual.

The individual response evaluation apparatus may further include: a light source unit; a reference beam generating unit which produces a reference beam; an object beam generating unit which produces an object beam; a CCD which combines the reference beam and the object beam to record a hologram; an arithmetic unit which numerically analyzes an interference fringe of the recorded hologram; a display unit which displays the digital hologram numerically analyzed by the arithmetic unit; and a heart rate analysis unit which carries out heart rate analysis from the analyzed digital hologram, wherein the arithmetic unit may obtain a plurality of phase reproduction phases for the hologram recorded in the CCD, and calculate an amplitude and an angle therefrom and transfer calculations to the display unit, the display unit may select and display the corresponding digital hologram until analysis of all holograms recorded in the CCD is completed and then transfer the digital hologram to the heart rate analysis unit, and in the heart rate analysis, a heart rate per minute may be calculated from the most frequent heart rate.

The control unit may adjust a distance between the lower fixing unit and the upper fixing unit to a ratio of 0.87 to 0.95, preferably 0.92 to 0.95 relative to a height of the individual to be measured. By adjusting the individual to the ratio, the individual may be efficiently fixed between the lower fixing unit and the upper fixing unit, without affecting metabolism such as blood circulation of the individual.

The individual response evaluation apparatus may measure one or more data selected from the group consisting of a real time heart rate of an aquatic organism, a spaced distance between the lower fixing unit and the upper fixing unit, a real time display of a heart rate phase, and a relaxation heart rate at the same time.

The data measured at the same time by the individual response evaluation apparatus may be accumulated by iterative learning by applying an artificial intelligence method.

It may be used for predicting a heart rate change in a higher organism by the iterative learning.

The chamber which is a core element of the individual response evaluation apparatus is described in more detail by the drawings.

The individual response evaluation apparatus of FIG. 2 according to the present invention allows an aquatic organism to be fixed between a lower structure unit 110 and an upper structure unit 120 in a chamber 100, and the upper structure unit is fixed in a form of being closely adhered to the aquatic organism by being moved up and down so that the aquatic organism is not moved within a range of not affecting heart rate measurement of the aquatic organism by a control unit 130.

The lower structure unit 110 and the upper structure unit 120 are formed of a material which an object beam may transmit and light transmission for hologram production is performed.

The light source unit is, though it is not shown in the drawing, installed in a lower region of the chamber or a lower region of the lower structure unit to provide an object beam generating unit (first light source) which irradiates the fixed individual with the object beam and a reference beam generating unit (second light source) which irradiates an optical path of the object beam with the reference beam. As the first light source and the second light source, a laser may be used as an example, but the present invention is not limited thereto, and a range of the wavelength of the laser is not limited as long as a normal hologram is formed and as an example, a laser of 633.2 nm may be used.

At a point where the optical paths of the object beam and the reference beam cross each other, a beam splitter is installed, thereby producing an optical interference signal from the object beam and the reference beam which transmits the individual and an objective lens. Since the beam splitter is a beam splitter which was conventionally used in a digital holography microscope for producing the optical interference signal between the object beam and the reference beam, the detailed description thereof will be omitted.

In an upper side of the beam splitter, a unit for taking the optical interference signal is installed, and as an example, a CCD camera may be used, but the present invention is not limited thereto.

FIG. 3 is illustrative of the individual response evaluation apparatus according to the present invention, and represents a real time heart rate monitoring system using extra-axial digital holography.

(A) represents a schematic diagram of an extra-axial digital holography setting based on a Mach-Zehnder interometer, and as a light source, a wavelength of 633.2 nm helium-neon (He—Ne) laser (Thorlabs) having a power of 5 mW is used. The objective lens (micro objective lens; 10×/N.A. 0.30, Olympus, UMPLFLN 10XW) is used in an underwater immersion form and has an operation distance of 3.5 mm.

A CCD camera (aca2040-180 km, Basler) taking the optical interference signal of the object beam and the interference beam is set to a resolution of 2048×2048 and a pixel size of 5.5 um×5.5 um as a factory setting, and is connected to a data acquisition device and used for taking for an exposure time of 2.5 ms.

Example

Immersion and Fixation of Water Flea in Chamber

A chamber having a schematic diagram like (B) of FIG. 3 and a digital holography device were connected and the individual response evaluation apparatus according to the present invention which was implemented as in (C) was used to test a toxic reaction for a water flea.

A water flea was carefully disposed between a lower structure unit 110 and an upper structure unit 120 of a chamber 100 carrying agarose gel (Sigma-Aldrich) (or other media may be replaced), a control unit 130 was operated to measure the height of the water flea, and the height of the upper structure unit was controlled to be positioned so as to be 0.95% of the height of the water flea. Here, the height of the water flea was measured as 538 um.

Generation of Heart Rate Signal Using Digital Holography Microscope

In the individual response evaluation apparatus, an extra-axial digital holography method was used to take a hologram of the water flea with a CCD camera.

The results are illustrated in FIG. 4.

The image was set to a pixel size of 0.5 um×0.5 um and a 8-bit resolution of 1024×1024 and taken. A maximum signal intensity ratio of the heart area represented by an orange dotted circle was measured as 0.047 (SR<5%). A k-space image by 2D Fourier transform of an interference image was obtained ((B) of FIG. 4), and an object wave-field intensity distribution which was numerically reconstructed at 7.6 um from the hologram was secured. Here, the reconstructed algorithm used an angle spectrum method ((C) of FIG. 4). (D) of FIG. 4 represents object wave-field intensity distributions of a numerically reconstructed object (above) and a reference taken without a water flea (below).

A phase distribution of the water flea was obtained after combining an object wave-field in the reference wave field ((E) of FIG. 4). The phase at this time covered a range from $-\pi$ to $+\pi$ Since a spatial phase is proportional to a specimen thickness and a refractive index, the time-resolved relative phase distribution of a water flea heart area was obtained therefrom and is represented by an orange rectangle ((F) to (H) of FIG. 4).

Analysis of Heart Rate of Water Flea Using Reconstructed Time-Resolved Phase Distribution The heart rate of the water flea was analyzed by the reconstructed time-resolved phase distributions, from the heart rate signal obtained by the method.

Figure 5A:
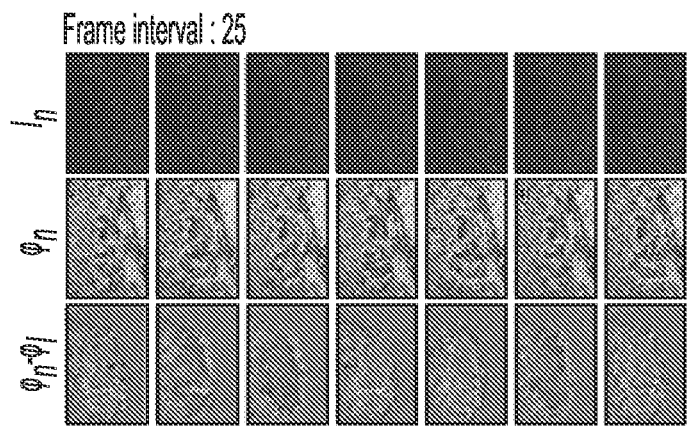
FIGS. 5A-5C are a heart rate analysis of a water flea using reconstructed time-resolved phase distribution, with the individual response evaluation apparatus for real time measurement of a heart rate of an aquatic organism according to the present invention.
Figure 5B:
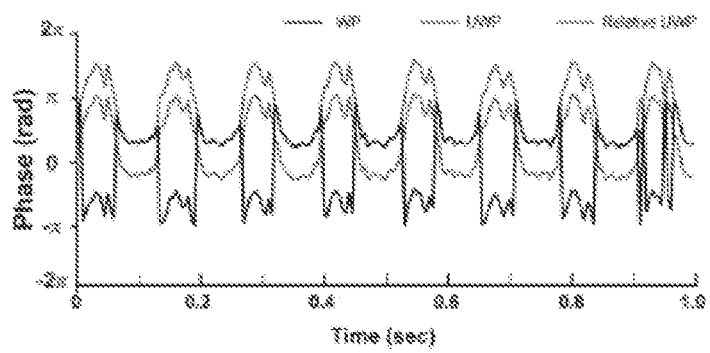
Figure 5C:
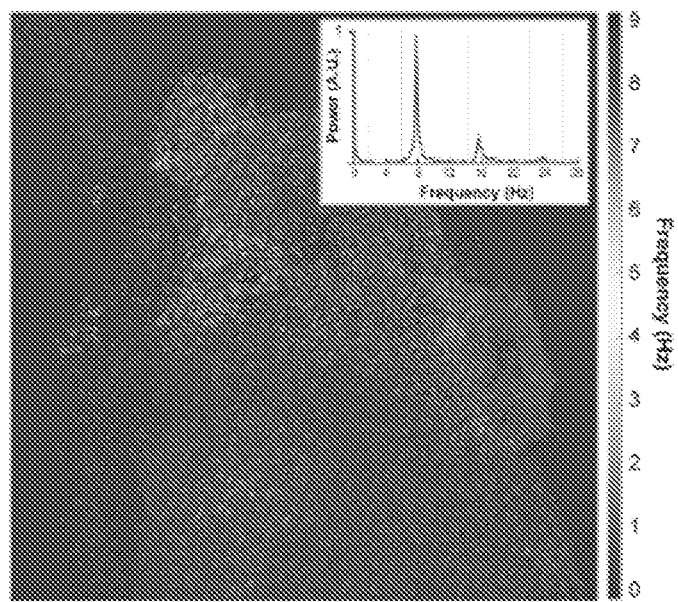

The results are illustrated in FIG. 5.

Time-resolved image sets were compared from intensity (above), phase (middle), and relative phase (below) distributions at 25 frame intervals ((A) of FIG. 5). According to the results, the appearance of the water flea may be more clearly recognized in a space phase map than in the hologram, but it is more difficult to divide a heart area in the space phase map than in the hologram.

Then, wrapped (WP), unwrapped (UWP), and relative unwrapped phases in the time-resolved one-dimensional heart rate signal were compared ((B) of FIG. 5). According to the results, the heart area is more clearly seen, which is presumed to be due to disappearance of the space phase of a carapace, by fixing the water flea between the lower structure unit 110 and the upper structure unit 120 of the chamber at 95% of the height of the water flea.

A Fourier spectrum method was used for evaluating periodic characteristics in heart rate analysis. In (C) of FIG. 5, a one-dimensional Fourier spectrum method was used for each pixel of 1000 frame sets to calculate a two-dimensional frequency distribution of the water flea. The drawing included inside is a Fourier spectrum plot at a point having 7.8 Hz (white arrow), and the heart rate for 5 seconds was 38.

Implement of Real Time Digital Holography Monitoring System

A high performance computing system to allow observation of a real time digital holography was constructed, so as to be consistent with the frame rate of the heart rate processing device as in Example 1.

To this end, a digital holography reconstruction algorithm was developed by a convolution method based on a fast Fourier transform (FFT) arithmetic operation performed in three steps.

Figure 6:
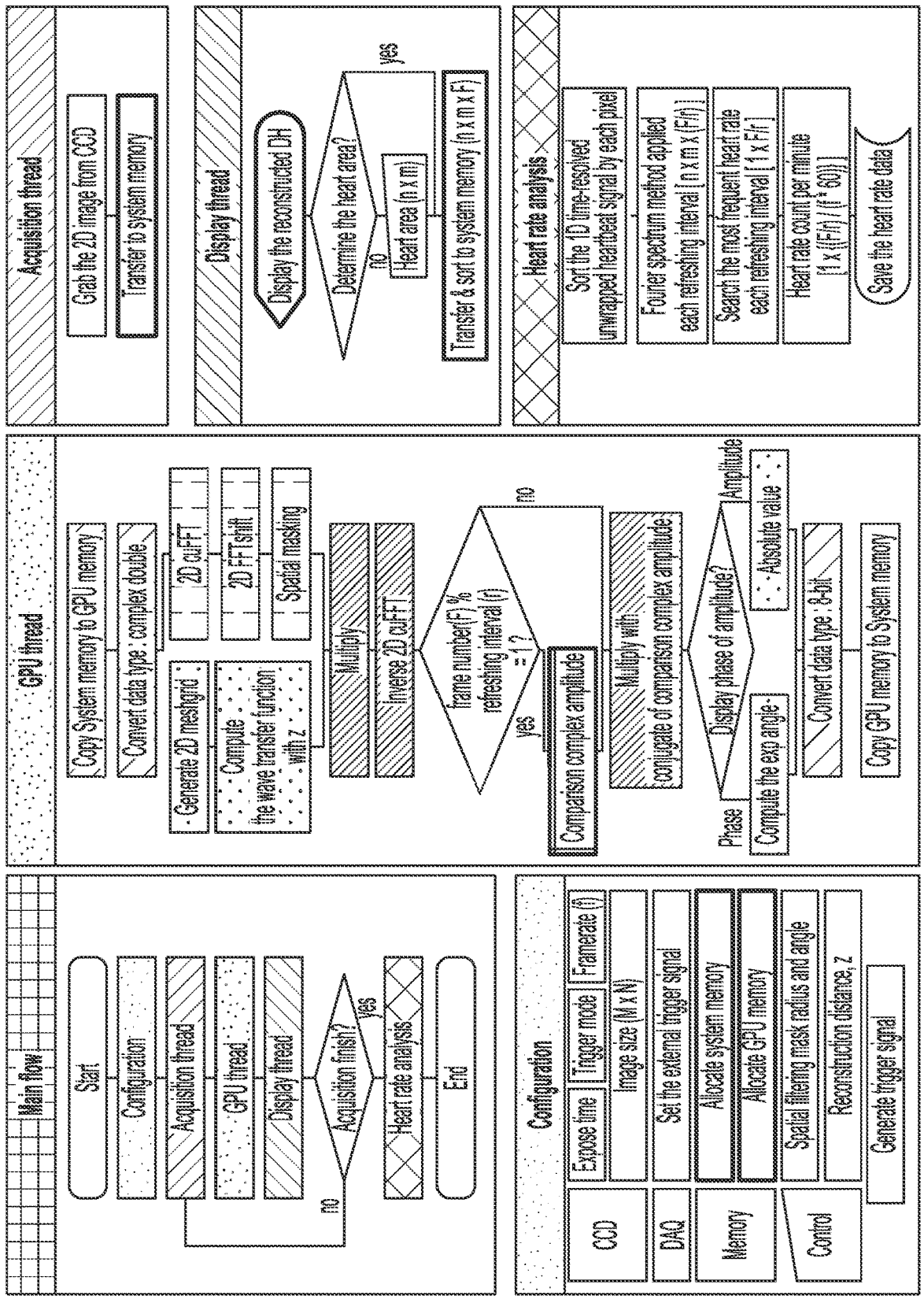
FIG. 6 is a detailed process by step of a flow chart for the method of evaluating an individual response by real time measurement of a heart rate of an aquatic organism according to the present invention.
Figure 7A:
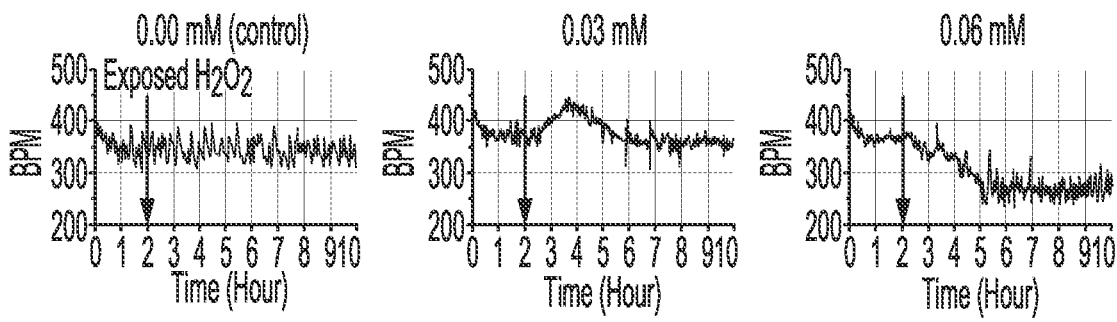
FIGS. 7A-7D are results of measuring a heart rate of a water flea 2 hours after treatment with 0.00 mM (blue), 0.03 mM (orange), and 0.06 mM (red) of hydrogen peroxide, by the method of evaluating an individual response by real time measurement of a heart rate of an aquatic organism according to the present invention.
Figure 7B:
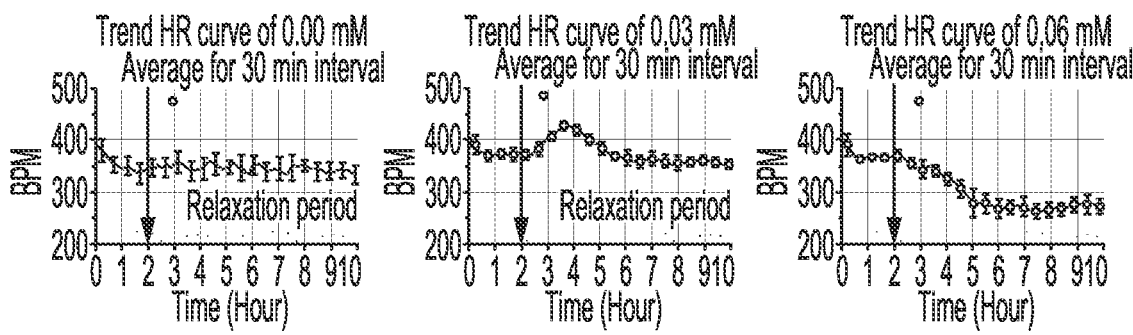
Figure 7C:
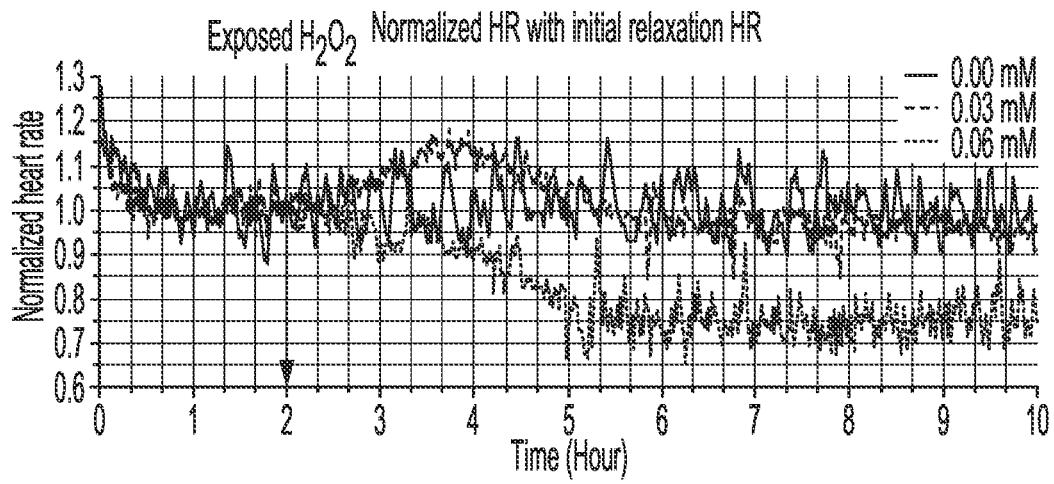
Figure 7D:
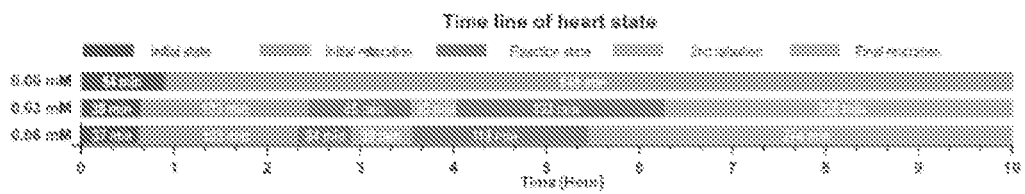
Figure 9A:
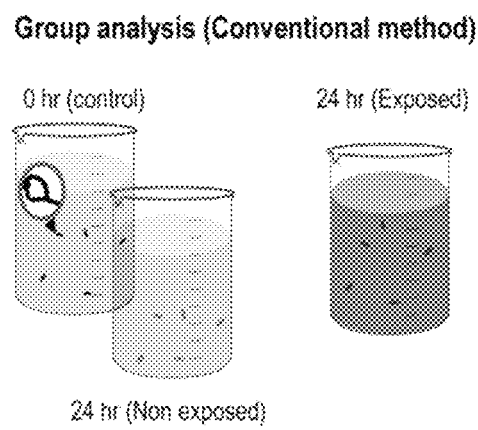
FIGS. 9A and 9B are results of comparison of a difference between the method of evaluating an individual response by real time measurement of a heart rate of an aquatic organism according to the present invention and a commonly used conventional method.
Figure 9B:
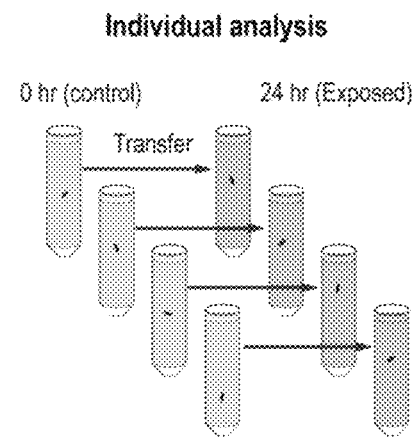

The algorithm allowed provision of a graphical user interface (GUI) to display the two-dimensional time-resolved relative phase map in real time and storage of the heart rate signal by high-speed arithmetic operation using a graphical processing unit (GPU) (see FIG. 6).

The arithmetic operation using GPU maximized a processing time by a parallel computing arithmetic operation method using a CUDA FFT library (cuFFT) supported by NVIDIA. This allowed real time display of the processed time-resolved relative phase map.

The performance of the real time digital holography monitoring system is shown in the following Table 1.

[Table 1] Performance of real time digital holography monitoring system

| Processing | Thread per block | Average duration (μs) |
|---|---|---|
| Transfer memory,/(CPU → GPU) | | 601.96 |
| Data type conversion (8-bit → 64-bit) | 1024 ×1024 | 24.74 |
| 2D cuFFT calculation, F(I(x, y)) | 32 × 32 | 2.35 |
| 2D FFTshift calculation, $F_s(I(x, y))$ | 32 × 32 | 11.57 |
| Calculation of product of $F_s(I(x, y))$ and space mask H (x, y) | 1 × 1024 | 4.31 |
| Production of transfer function T (x, y) | 32 × 32 | 3.64 |
| Calculation of product of T (x, y) and H (x, y) | 1024 × 1024 | 2.99 |
| Calculation of product of conjugated comparison complex amplitude | 1024 × 1024 | 2.89 |
| Calculation of 2D invert cuFFT | 32 × 32 | 3.35 |
| Data type conversion (64-bit → 8-bit) | 1024 × 1024 | 5.69 |
| Transfer memory (GPU → CPU) | | 1068.37 |
| Total | | 1731.84 |

* represents an average GPU processing time using 1000 frames of a time-resolved spatial phase image in the above table. A GPU processing time was measured using NVIDIA Nsight Compute.

In addition, in the present invention, unlike a conventional digital holography method in need of information of total interferometric image sets, only a time-resolved heart beat signal is needed, thereby achieving a surprising space saving effect that a size per hour of a data storage area required for storing the same heart rate signal of the heart area having a size of 10×10 pixels is decreased from 703 GB/hr to 3.43 MB/hr by 200,000 times or more, from which a new effect to allow digital holography to be monitored in real time for a long time was obtained.

Heart Rate Monitoring of Water Flea Depending on Exposure to Hydrogen Peroxide ($H_2O_2$)

In the Example, a water flea was fixed to a chamber 100 carrying a 90 mL of M4 medium in the manner described above, and then observed.

2 hours after the observation, 19 mL of hydrogen peroxide having concentrations of 0.00 mM, 0.03 mM, and 0.06 mM, respectively was each mixed for each experiment to perform the experiment repeatedly so that the water flea is exposed to the hydrogen peroxide. At this time, in a negative control group of 0.00 mM treatment, 10 mL of an M4 medium was further mixed for unifying volume.

Upon observation, the heart rate analysis was performed by dividing the section into those before and after exposure to hydrogen peroxide.

FIG. 7 illustrates the results.

In order to express the heart rate trend of (B) of FIG. 7, in (A) of FIG. 7, an original heart rate (OHR) was flattened every 30 minutes by a moving average method.

As a result of measuring a standard deviation (unit: BPM, beat per minute) between the heart rate and OHR for each test group, it was confirmed that the standard deviation was shown as 18 BPM, 11 BPM, and 14 BPM for each concentration of hydrogen peroxide. (C) of FIG. 7 is results of performing normalization for initial RHR, which are the results of measuring the heart rate change depending on the exposure to a toxic substance for evaluating toxicity to the heart. For the samples treated with 0.03 mM and 0.06 mM hydrogen peroxide excluding a negative control group, respectively, as a result of measuring final RHR, it was confirmed that the heart rate relative to the original heart rate (OHR) was decreased to 3.3% (−13 BPM) and 22.7% (−109 BPM).

As a result of comparing the heart rate by normalization, the negative control group had the same final RHR as OHR, while in the two test groups treated with hydrogen peroxide, a decrease in the heart rate was confirmed.

As a result of measuring significance of the decrease by applying a t-test method to the normalized results, the test group treated with 0.03 mM hydrogen peroxide represented a F value of 0.89, thereby representing heteroscedasticity of variance and a significance probability more than 0.05. It was confirmed therefrom that the t-test results in which uneven variance is presumed was less than 0.01 and the final RHR showed a significant difference as compared with OHR when treated with 0.03 mM hydrogen peroxide.

In the present invention, measurement of each experiment group was performed at the same time for three water flea test groups, and the relaxation heart rate measurement results for the negative control group and the hydrogen peroxide treated test group are summarized in the following Table 2.

TABLE 2

Results of measuring relaxation heart rate (RHR) depending on test group

| Hydrogen peroxide concentration (mM) | # | 0 hr (BPM) | 24 hr (BPM) | P-value (95% confidence interval) relative to 0 hr | relative to 0 mM group | Normalization relative to 0 hr (%) | P-value relative to normalized 0.00 group (95% confidence interval) |
|---|---|---|---|---|---|---|---|
| 0.00 | 1 | 308.92 ± 13.25 | 313.58 ± 23.69 | 0.052 | | 101.51 ± 7.67 | — |
| | 2 | 325.55 ± 8.24 | 328.98 ± 15.50 | 0.051 | | 101.05 ± 4.76 | |
| | 3 | 368.16 ± 6.55 | 363.78 ± 14.45 | 0.013 | | 98.81 ± 3.92 | |
| | Group | 334.21 ± 26.84 | 335.44 ± 27.86 | 0.256 | | 100.44 ± 5.45 | |
| 0.03 | 4 | 363.22 ± 12.11 | 328.43 ± 18.01 | p0.03 < 0.001 | 0.069 | 90.42 ± 4.74 | p0.03n < 0.001 |
| | 5 | 350.78 ± 20.23 | 339.28 ± 6.54 | | 0.292 | 96.72 ± 1.78 | |
| | 6 | 486.43 ± 6.63 | 353.28 ± 27.98 | | <0.001 | 91.42 ± 6.94 | |
| | Group | 366.81 ± 20.43 | 340.33 ± 21.98 | | 0.217 | 92.84 ± 5.60 | |
| 0.06 | 7 | 370.07 ± 25.38 | 274.82 ± 16.01 | p0.06 < 0.001 | <0.001 | 74.26 ± 4.33 | p0.06n < 0.001 |
| | 8 | 378.43 ± 15.41 | 299.47 ± 14.70 | | | 79.13 ± 3.88 | |
| | 9 | 383.90 ± 13.02 | 262.87 ± 7.41 | | | 68.47 ± 1.93 | |
| | Group | 383.81 ± 12.99 | 279.05 ± 12.71 | | | 73.96 ± 5.61 | |

*N: Number of samples (specimens) per group = 3, n: Average per minute for 1 hour = 6-
**The RHR represents an average heart rate per minute for 1 hour (n = 60), and p-value was evaluated by two sample t-tests in which unequal variances are presumed in a 95% confidence interval. The results were average ± standard deviation (SD).

From the results, as a result of performing the t-test of the result of treatment with 0.06 mM hydrogen peroxide as in the case of treatment with 0.03 mM, a value less than 0.01 was obtained, and it was confirmed therefrom that the final RHR represented a significant difference relative to OHR even with treatment with 0.06 mM.

FIG. 8 illustrates results of analyzing average RHR for the exposure groups of Table 2. As a result of normalized comparison of (A) of FIG. 8, it was shown that the difference was not significant, but in (B) and (C) of FIG. 8 after performing normalization, it was confirmed that only a heart rate increase of 0.42% occurred after 24 hours in the negative control group, while a heart rate decrease of 7.16% and 25.97% occurred after 24 hours in the 0.03 mM and 0.06 mM-treated test groups.

(d) of FIG. 8 is a result of measuring a reactive oxygen species (ROS) level following hydrogen peroxide treatment. As a result, it was confirmed that the 0.06 mM-treated test group showed the level 7.8 times higher than the 0.03 mM-treated group, and a significantly increased reactive oxygen species level was shown. A correlation between a heart rate decrease and a reactive oxygen species level depending on hydrogen peroxide exposure was verified by measuring the reactive oxygen species level.

The description of the suggested examples is provided so that any person with ordinary skill in the art may use or carry out the present invention. Various modifications of the examples will be apparent to a person skilled in the art, and general principles defined here may be applied to other examples without departing from the scope of the present invention. Thus, the present invention is not limited by the examples suggested herein, but should be construed in the widest sense consistent with the principles and new characteristics suggested herein.

The method of evaluating an individual response by real time measurement of a heart rate of an aquatic organism and the individual response evaluation apparatus by real time measurement of a heart rate of an aquatic organism may effectively fix the aquatic organism so that it does not move without affecting the living body of an aquatic organism, for real time measurement of the heart rate of an aquatic organism, and may measure the heart rate using digital holography to display the heart rate while configuring a data format to allow the corresponding data to be stored for a long time, whereby after the individual is treated with a compound for inducing an individual response and a heart rate change is secured in real time by image processing, the presence or absence of harmfulness due to induction of the individual response may be effectively determined.

The invention claimed is:

1. A method of evaluating an individual response by real time measurement of a heart rate of an aquatic organism which is a method of evaluating an individual response using digital holography, the method comprising:
   (a) disposing the aquatic organism between a lower fixing unit fixed to a lower end inside a chamber and an upper fixing unit which is spaced apart from the lower fixing unit and is movable in a direction of the lower fixing unit or in an opposite direction thereof so that the aquatic organism is immersed in a culture fluid to which a compound for inducing an individual response is added, adhering the upper fixing unit to the aquatic organism to measure a height of the aquatic organism, and then adjusting a position of the upper fixing unit to fix the aquatic organism;
   (b) continuously measuring a digital hologram for the aquatic organism; and
   (c) restoring the digital hologram obtained by the measurement to calculate a heart rate change, and determining therefrom whether the individual response is caused by the compound for inducing an individual response,
   wherein an algorithm for restoration further includes displaying a 2D-time-resolved relative phase map in real time and storing the heart rate at the same time, and
   wherein the heart rate is obtained by an analysis method including:
   a) selecting pixels corresponding to a heart area in a secured digital hologram;
   b) applying a Fourier spectrum method to each refreshing interval;
   c) searching a most frequent heart rate in each refreshing interval; and
   d) calculating a heart rate per minute from the most frequent heart rate.

2. The method of evaluating an individual response by real time measurement of a heart rate of an aquatic organism of claim 1, wherein after the position of the upper fixing unit is adjusted and fixed, a distance between the lower fixing unit and the upper fixing unit is a ratio of 0.87 to 0.95 relative to the height of the aquatic organism.

3. The method of evaluating an individual response by real time measurement of a heart rate of an aquatic organism of claim 2, wherein after the position of the upper fixing unit is adjusted and fixed, a distance between the lower fixing unit and the upper fixing unit is a ratio of 0.92 to 0.95 relative to the height of the aquatic organism.

4. The method of evaluating an individual response by real time measurement of a heart rate of an aquatic organism of claim 1, wherein the compound is an organic compound, a metal, acid-alkali, gas, a medicine, or a nanoparticle.

5. The method of evaluating an individual response by real time measurement of a heart rate of an aquatic organism of claim 4, wherein the compound is selected from dimethylformamide, methanol, methylisobutylketone, benzene, carbon tetrachloride, styrene, cyclohexane, acetone, acetaldehyde, isobutylalcohol, methyl chloride, ethylene glycol, xylene, toluene, toluene-2,4-diisocyanate, trichloroethylene, n-hexane, lead, nickel, manganese, mercury, zinc, aluminum, iron, cadmium, chromium, hydrogen peroxide, acetic acid, sodium hydroxide, hydrochloric acid, sulfuric acid, nitric acid, phosphoric acid, ammonia, chlorine, ozone, hydrogen sulfide, carbon monoxide, sulfur dioxide, nitrogen dioxide, medicines, gold nano, silver nano, single-walled carbon nanotubes (SWCNT), multi-walled carbon nanotube (MWCNT), fullerene ($C_{60}$), iron nanoparticles, carbon black, titanium dioxide, aluminum oxide, cerium oxide, zinc oxide, silicon dioxide, polystyrene, dendrimers, and nanoclay.

6. The method of evaluating an individual response by real time measurement of a heart rate of an aquatic organism of claim 4, wherein the aquatic organism is treated with the compound a concentration of 0.01 to 0.10 mM.

7. The method of evaluating an individual response by real time measurement of a heart rate of an aquatic organism of claim 1, wherein the heart rate change is obtained by calculating an original heart rate (OHR), and a relaxation heart rate (RHR) by the following Equation IV:

$$RHR = \frac{\sum_{j=t_i}^{t_f} OHR(j)}{t_f - t_i},\qquad \text{[Equation IV]}$$

wherein $t_i$ and $t_f$ refer to an initial time and a final time in a relaxation state.

8. An individual response evaluation apparatus by real time measurement of a heart rate of an aquatic organism, using digital holography, the apparatus comprising: a chamber carrying a culture fluid; a lower fixing unit; an upper fixing unit spaced apart from the lower fixing unit; and a control unit controlling a position of the upper fixing unit,
wherein the lower fixing unit is fixed to a lower end inside the chamber, an aquatic organism is disposed between the lower fixing unit and the upper fixing unit, the upper fixing unit is fixed to one side surface of the chamber and movable up and down, and the control unit adjusts the position of the upper fixing unit to fix the aquatic organism, after the upper fixing unit is adhered to the aquatic organism to measure the height the aquatic organism, the apparatus further comprising: a light source unit; a reference beam generating unit which produces a reference beam; an object beam generating unit which produces an object beam; a CCD which combines the reference beam and the object beam to record a hologram; an arithmetic unit which numerically analyzes an interference fringe of the recorded hologram; a display unit which displays the digital hologram numerically analyzed by the arithmetic unit; and a heart rate analysis unit which carries out heart rate analysis from the analyzed digital hologram,
wherein the arithmetic unit obtains a plurality of phase restoration phases for the hologram recorded in the CCD, and calculates an amplitude and an angle therefrom and transfers calculations to the display unit, the display unit selects and displays the corresponding digital hologram until analysis for all holograms recorded in the CCD is completed and then transfers the digital hologram to the heart rate analysis unit, and in the heart rate analysis, a heart rate per minute is calculated from the most frequent heart rate, and
wherein the heart rate is obtained by an analysis method including:
a) selecting pixels corresponding to a heart area in a secured digital hologram;
b) applying a Fourier spectrum method to each refreshing interval;
c) searching a most frequent heart rate in each refreshing interval; and
d) calculating a heart rate per minute from the most frequent heart rate.

9. The individual response evaluation apparatus by real time measurement of a heart rate of an aquatic organism of claim 8, wherein the control unit adjusts a distance between the lower fixing unit and the upper fixing unit to a ratio of 0.87 to 0.95 relative to a height of the aquatic organism.

10. The individual response evaluation apparatus by real time measurement of a heart rate of an aquatic organism of claim 9, wherein the control unit adjusts the distance between the lower fixing unit and the upper fixing unit to a ratio of 0.92 to 0.95 relative to the height of the aquatic organism.

11. The individual response evaluation apparatus by real time measurement of a heart rate of an aquatic organism of claim 8, using the digital holography, wherein the individual response evaluation apparatus allows measurement of one or more data selected from a group consisting of a real time heart rate of the aquatic organism, a spaced distance between the lower fixing unit and the upper fixing unit, a real time display of a heart rate phase, and a relaxation heart rate at the same time.

12. The individual response evaluation apparatus by real time measurement of a heart rate of an aquatic organism of claim 11, wherein the data measured at the same time by the individual response evaluation apparatus is accumulated by iterative learning by applying an artificial intelligence method.

13. The individual response evaluation apparatus by real time measurement of a heart rate of an aquatic organism of claim 12, wherein the individual response evaluation apparatus is used for predicting a heart rate change in the aquatic organism by the iterative learning.

* * * * *